United States Patent [19]

Robertson et al.

[11] Patent Number: 6,074,860

[45] Date of Patent: Jun. 13, 2000

[54] CATALASES

[75] Inventors: Dan E. Robertson, Haddonfield; Indrajit Sanyal, Maple Shade; Robert S. Adhikary, Cherry Hill, all of N.J.

[73] Assignee: Diversa Corporation, San Diego, Calif.

[21] Appl. No.: 08/951,844

[22] Filed: Oct. 16, 1997

Related U.S. Application Data

[62] Division of application No. 08/674,887, Jul. 3, 1996.
[51] Int. Cl.[7] ............................. C12N 9/08; C12N 15/53
[52] U.S. Cl. ........................................... 435/192; 536/23.2
[58] Field of Search ........................... 435/192; 536/23.2

[56] References Cited

PUBLICATIONS

H. Forkl et al., "Molecular Cloning, Sequence Analysis and Expression of the Gene for Catalase–Peroxidase (cpeA) from the Photosynthetic Bacterium *Rhodobacter capsulatus* B10", Eur. J. Biochem. 214:251–258.

S. Loprasert et al., Cloning, Nucleotide Sequence, and Expression in *Escherichia coli* of the *Bacillus stearothermophilus* Perioxidase Gene (perA).

M. Mutsuda et al. "The Catalase–Peroxidase of *Synechococcus* PCC 7942: Purification, Nucleotide Sequence Analysis and Expression in *Escherichia coli*", Biochem J. 316:251–257, May 1996.

*Primary Examiner*—Rebecca E. Prouty
*Attorney, Agent, or Firm*—Gray, Cary, Ware & Freidenrich, LLP

[57] ABSTRACT

Catalase enzymes derived from bacteria from the genera Alcaligenes (Deleya) and Microscilla are disclosed. The enzymes are produced from native or recombinant host cells and can be utilized to destroy or detect hydrogen peroxide, e.g., in production of glyoxylic acid and in glucose sensors, and in processes where hydrogen peroxide is used as a bleaching or antibacterial agent, e.g. in contact lens cleaning, in bleaching steps in pulp and paper preparation and in the pasteurization of dairy products.

2 Claims, 8 Drawing Sheets

FIG. 1A

Alcaligenes (Deleya) aquamarinus  Catalase - 64CA2

(SEQ ID NO: 5)
(SEQ ID NO: 6)

```
  1  ATG AAT AAC GCA TCC GCT GAC GAT CTA CAC AGT AGC TTG CAA AGA TGC AGA GCA TTT  60
  1  Met Asn Asn Ala Ser Ala Asp Asp Leu His Ser Ser Leu Gln Arg Cys Arg Ala Phe  20

61  GTT CCC TTG GTA TCG CCA AGG CAT AGA GCA ATA AGG GAG AGA GCT ATG AGC GGT AAA TGT 120
 21  Val Pro Leu Val Ser Pro Arg His Arg Ala Ile Arg Glu Arg Ala Met Ser Gly Lys Cys  40

121  CCT GTC ATG CAC GGT GGT AAC ACC TCG ACT GGT ACC TCC AAC AAA GAT TCC AAC CCG GAA 180
 41  Pro Val Met His Gly Gly Asn Thr Ser Thr Gly Thr Ser Asn Lys Asp Ser Asn Pro Glu  60

181  GGG TTG AAC CTG GAT ATT TTG CAT CAG CAA GAT CGC AAA TCA GAC CCG ATG CCG GAT 240
 61  Gly Leu Asn Leu Asp Ile Leu His Gln Gln Asp Arg Lys Ser Asp Pro Met Asp Pro Asp  80

241  TTC AAC TAC CGT GAA GTA CGC GAA GAG CTG CGC CTG AAG AAA GAT GTC CAC 300
 81  Phe Asn Tyr Arg Glu Val Arg Lys Leu Asp Ala Leu Lys Lys Asp Val His 100

301  GCG TTG ATG ACC GAT AGC CAA GAG TGG CCC GAT GAC TGG GGG CAC TAC GGC GGT TTG 360
101  Ala Leu Met Thr Asp Ser Gln Glu Trp Pro Asp Asp Trp Gly His Tyr Gly Gly Leu 120

361  ATG ATC CGT ATG GCT TGG CAC TCC GCT ATT GCT GAT GGC CGT GGG GGC 420
121  Met Ile Arg Met Ala Trp His Ser Ala Ile Ala Asp Gly Arg Gly Gly 140

421  GGT GGT ACC GGA AGC CAG CGC CGT TTA CCG TGG CCA CCG GAC AAC GTC AGC CTG 480
141  Gly Gly Thr Gly Ser Gln Arg Arg Leu Pro Trp Pro Pro Asp Asn Val Ser Leu 160

481  GAT AAA GCG CGC GAC CTG ATG ATT CTG GCT GGA TAC AAG AAG TAC GGC AAC AAA ATC AGC TGG 540
161  Asp Lys Ala Arg Asp Leu Met Ile Leu Ala Gly Tyr Lys Lys Tyr Gly Asn Lys Ile Ser Trp 180

541  GCA GAC CTG ATG CTT ATG ATT CTG GCT ACC GTG GCT TAT GAG TCC ATG GGC TTA CCT GCT TAC 600
181  Ala Asp Leu Met Leu Met Ile Leu Ala Thr Val Ala Tyr Glu Ser Met Gly Leu Pro Ala Tyr 200

601  GGC TTC TCT TTC GGC CGC GTC GAT ATT TGG GAA AAA GAT ATC TAC TGG GGT GAC 660
201  Gly Phe Ser Phe Gly Arg Val Asp Ile Trp Glu Lys Asp Ile Tyr Trp Gly Asp 220
```

FIG. 1B

```
 661 GAA AAA GAG TGG CTG GCA CCT TCT GAC GAA CGC TAC GGC GAC GTG AAC AAG CCA GAG ACC  720
 221 Glu Lys Glu Trp Leu Ala Pro Ser Asp Glu Arg Tyr Gly Asp Val Asn Lys Pro Glu Thr  240

721 ATG GAA AAC CCG CTG GCG GCT GTC CAA ATG GGT CTG ATC TAT GTG AAC CCG GAA GGT GTT  780
 241 Met Glu Asn Pro Leu Ala Ala Val Gln Met Gly Leu Ile Tyr Val Asn Pro Glu Gly Val  260

781 AAC GGC CAC CCT GAT CCG CTG AGA ACC GCA CAG CAG GTA CTT GAA ACC TTC GCC CGT ATG  840
 261 Asn Gly His Pro Asp Pro Leu Arg Thr Ala Gln Gln Val Leu Glu Thr Phe Ala Arg Met  280

841 GCG ATG AAC GAC GAA AAA GAC GGT CTG ACA GCC CTC ACA GCT GGC GGC CAC GTC GGT AAT TGT  900
 281 Ala Met Asn Asp Glu Lys Thr Ala Leu Thr Ala Gly Gly His Val Gly Asn Cys  300

901 CAC GGT AAT GCC TCT GCG TTA GCC CCT GAC GCC CCA AAA GCC TCT GAC GTT GAA AAC  960
 301 His Gly Asn Ala Ser Ala Leu Ala Pro Asp Ala Pro Lys Ala Ser Asp Val Glu Asn  320

961 CAG GGC TTA GGT TGG GGC TTA GGT CTG AAC ATG CAG GGC AAG GCA AGC AAC GCC GTG ACC TCG 1020
 321 Gln Gly Leu Gly Trp Gly Asn Met Gln Gly Lys Ala Ser Asn Ala Val Thr Ser  340

1021 GGT ATC GAA GGT GCT TGG ACC ACC AAC CCC ACG AAA TTC GAT ATG GGC TAT TTC GAC CTG 1080
 341 Gly Ile Glu Gly Ala Trp Thr Thr Asn Pro Thr Lys Phe Asp Met Gly Tyr Phe Asp Leu  360

1081 CTG TTC GGC TAC AAT TGG GAA CTG CTG AAA AAG AGT CCT GGT GCC CAC CAT TGG GAA CCG 1140
 361 Leu Phe Gly Tyr Asn Trp Glu Leu Leu Lys Lys Ser Pro Gly Ala His His Trp Glu Pro  380

1141 ATT GAC ATC AAA AAG GAA AAC AAG CCG GTT GAC GCC GCA AGC GAC CCC TCT ATT CGC CAC AAC 1200
 381 Ile Asp Ile Lys Lys Glu Asn Lys Pro Val Asp Ala Ser Asp Pro Ser Ile Arg His Asn  400

1201 CCG ATC ATG ACC GAT GCG GAT ATG GCC ATA AAG GTA AAT CCG ACC TAT CGC GCT ATC TGC 1260
 401 Pro Ile Met Thr Asp Ala Asp Met Ala Ile Lys Val Asn Pro Thr Tyr Arg Ala Ile Cys  420

1261 GAA AAA TTC ATG GCC GAT CCT GAG TAC TTC AAG AAA ACT TTC GCG AAG GCG TGG GCA TGG TTC AAG 1320
 421 Glu Lys Phe Met Ala Asp Pro Glu Tyr Phe Lys Lys Thr Phe Ala Lys Ala Trp Phe Lys  440

1321 CTG ACG CAC CGT GAC CTG GGC CCG AAA TCA CGT TAC ATC GGC CCG GAA GTG CCG GCA GAA 1380
 441 Leu Thr His Arg Asp Leu Gly Pro Lys Ser Arg Tyr Ile Gly Pro Glu Val Pro Ala Glu  460
```

FIG. 1C

```
1381 GAC CTG ATT TGG CAA GAC CCG ATT CCG GCA GGT AAC ACC GAC TAC TGC GAA GAA GTG GTC 1440
 461 Asp Leu Ile Trp Gln Asp Pro Ile Pro Ala Gly Asn Thr Asp Tyr Cys Glu Glu Val Val  480

1441 AAG CAG AAA ATT GCA CAA AGT GGC CTG AGC ATT AGT GAG ATG GTC TCC ACC GCT TGG GAC 1500
 481 Lys Gln Lys Ile Ala Gln Ser Gly Leu Ser Ile Ser Glu Met Val Ser Thr Ala Trp Asp  500

1501 AGT GCC CGT ACT TAT CGC GTT TCC GAT ATG CGC GGT GCT AAC GGT GCT CGC ATT CGC 1560
 501 Ser Ala Arg Thr Tyr Arg Val Ser Asp Met Arg Gly Ala Asn Gly Ala Arg Ile Arg  520

1561 TTG GCC CCA CAG AAC GAG TGG CAG GGC CTG GCG CGC AAA GTG CTG AGC GCC 1620
 521 Leu Ala Pro Gln Asn Glu Trp Gln Gly Leu Ala Arg Lys Val Leu Ser Ala  540

1621 GTC TAC GAG CAG ATC TCT GCC GAC AGC ATC GCG GCT AGC GTT CTG GCC 1680
 541 Val Tyr Glu Gln Ile Ser Ala Asp Ser Ile Ala Asp Val Ile Val Leu Ala  560

1681 GGT AGC GTA GGC ATC GAG GTA AAA GCA GGT TAC GAT GTG CGC GTT CCC TTC 1740
 561 Gly Ser Val Gly Ile Glu Val Lys Ala Ala Gly Tyr Asp Val Arg Val Pro Phe  580

1741 CTG AAA GGC CGT GAT GCG GAT ACC GAG ATG GCA GAC TCC TTC GCA CCG CTG 1800
 581 Leu Lys Gly Arg Asp Ala Asp Thr Glu Met Ala Asp Ser Phe Ala Pro Leu  600

1801 GAG CCG CTG GCC GAT GGC TTC CGC AAC TGG CAG AAA AAA GAG TAT GTG GTG AAG CCG GAA 1860
 601 Glu Pro Leu Ala Asp Gly Phe Arg Asn Trp Gln Lys Lys Glu Tyr Val Val Lys Pro Glu  620

1861 GAG ATG CTG CTG GAT CGT ATG CGG GCA CAG CTG ATG CGC TTA ACC GGC ATG ACC GTG CTG 1920
 621 Glu Met Leu Leu Asp Arg Met Arg Ala Gln Leu Met Arg Leu Thr Gly Met Thr Val Leu  640

1921 CTG GGT GGT ATG GAA GGC CAG CTG GGC ACC TAT GGT AAA CAC GGC GTA TTC ACC 1980
 641 Leu Gly Gly Met Glu Gly Gln Leu Gly Thr Tyr Gly Lys His Gly Val Phe Thr  660

1981 GAT TGT GAA GGC CAG TTG CAG CTG ACC AAC GAC TTT TTT GTT AAC CTG ACC GAT ATG GGG AAC AGC 2040
 661 Asp Cys Glu Gly Gln Leu Gln Leu Thr Asn Asp Phe Phe Val Asn Leu Thr Asp Met Gly Asn Ser  680

2041 TGG AAG CCG GTA GGT GCC GAC TAC AGC AAC GCC CGC GAA ATC CGC GAT CGC AAG ACC GGT GCC GTG AAG 2100
 681 Trp Lys Pro Val Gly Ala Asp Tyr Ser Asn Ala Arg Glu Ile Arg Asp Arg Lys Thr Gly Ala Val Lys  700
```

FIG. 1D

```
2101 TGG ACC GCC TCG CGG GTG GAT CTG GTA TTT GGT TCC AAC TCG CTA CTG CGC TCT TAC GCA 2160
 701 Trp Thr Ala Ser Arg Val Asp Leu Val Phe Gly Ser Asn Ser Leu Leu Arg Ser Tyr Ala  720

2161 GAA GTG TAC GCC CAG GAC GAT AAC GGC GAG AAG TTC GTC AGA GAC TTC GTC GCC TGG 2220
 721 Glu Val Tyr Ala Gln Asp Asp Asn Gly Glu Lys Phe Val Arg Asp Phe Val Ala Ala Trp  740

2221 ACC AAA GTG ATG AAC GCC GAC CGT TTC GAC GTC GCG TCG TAA 2262
 741 Thr Lys Val Met Asn Ala Asp Arg Phe Asp Val Ala Ser End  754
```

FIG. 2A

Microscilla furvescens Catalase - 53CA1

(SEQ ID NO:7)
(SEQ ID NO:8)

```
  1  ATG GAA AAT CAC AAA CAC TCA GGA TCT TCT ACG TAT AAC ACA AAC ACT GGC GGA AAA TGC   60
  1  Met Glu Asn His Lys His Ser Gly Ser Ser Thr Tyr Asn Thr Asn Thr Gly Asn Lys Cys   20

61  CCT TTT ACC GGA GGT TCG CTT AAG CAA AGT GCA GGT GGC ACC AAA AAC AGG GAT TGG       120
 21  Pro Phe Thr Gly Gly Ser Leu Lys Gln Ser Ala Gly Gly Thr Lys Asn Arg Asp Trp       40

121  TGG CCC AAC ATG CTC AAC CTC GGC ATC TTA CGC CAA CAT TCA CGA CTA TCG GAC CCA AAC  180
 41  Trp Pro Asn Met Leu Asn Leu Gly Ile Leu Arg Gln His Ser Arg Leu Ser Asp Pro Asn   60

181  GAC CCG GAT TTT GAC TAT GCC GAA GAG TTT AAG AAG CTA GAT CTG GCA GCG GTT AAA AAG  240
 61  Asp Pro Asp Phe Asp Tyr Ala Glu Glu Phe Lys Lys Leu Asp Leu Ala Ala Val Lys Lys   80

241  GAC CTG GCA GCG CTA ATG ACA GAT CTG ATG GCG TGG TCA CAG GCC TGG TGG CAT TAT GGC  300
 81  Asp Leu Ala Ala Leu Met Thr Asp Leu Met Ala Trp Ser Gln Ala Trp Trp His Tyr Gly  100

301  GGC CCC TTC TTT ATA CGC ATG GGT GGC ATG GCG TTC CGC TTC ACC TAC CGT GGT GAT GGC  360
101  Gly Pro Phe Phe Ile Arg Met Gly Gly Met Ala Phe Arg Phe Thr Tyr Arg Gly Asp Gly  120

361  CGT GGT GGC GAT AAA GCA CGC TCC GGC TCA CAG CGC TTC CTT TGG CCT CTC AAT AGC TGG  CCA GAC AAT  420
121  Arg Gly Gly Asp Lys Ala Arg Ser Gly Ser Gln Arg Phe Leu Trp Pro Leu Asn Ser Trp Pro Asp Asn  140

421  GCC AAT CTG GAT AAA GCA CGC TTG CTT CTT CTT TGG CCC ATC AAA CAA TAC GGT CGA AAA  480
141  Ala Asn Leu Asp Lys Ala Arg Leu Leu Leu Leu Trp Pro Ile Lys Gln Tyr Gly Arg Lys  160

481  ATC TCC TGG GCG GAT CTA ATG ATA CTC ACA GGA AAC GTA GCT CTG GAA GCT ATG GGC TTT  540
161  Ile Ser Trp Ala Asp Leu Met Ile Leu Thr Gly Asn Val Ala Leu Glu Thr Met Gly Phe  180

541  AAA ACT TTT GGT GCA GGT GGC AGA GGA GCA GAT GTA TGG GAG CCT GAG GAA GAT GTA TAC  600
181  Lys Thr Phe Gly Ala Gly Gly Arg Gly Ala Asp Val Trp Glu Pro Glu Glu Asp Val Tyr  200

601  TGG GGA GCA GAA ACC GAA GAA TGG CTG GGA GAC AAG CGC TAT GAA GGT GAC GAC CGA GAG  660
201  Trp Gly Ala Glu Thr Glu Glu Trp Leu Gly Asp Lys Arg Tyr Glu Gly Asp Asp Arg Glu  220
```

FIG. 2B

```
 661 AAT CCC CTG GGA GCC GTA CAA ATG GGA CTC ATC TAT GTA AAC CCC GAA GGA CCC AAC GGC  720
 221 Asn Pro Leu Gly Ala Val Gln Met Gly Leu Ile Tyr Val Asn Pro Glu Gly Pro Asn Gly  240

721 AAG CCA GAC CCT ATC GCT GCT GCG CGT GAT ATT CGT GAG ACT TTT GGC CGA ATG GCA ATG  780
 241 Lys Pro Asp Pro Ile Ala Ala Ala Arg Asp Ile Arg Glu Thr Phe Gly Arg Met Ala Met  260

781 AAT GAC GAA GAA ACC GTG GCT CTC ATA GCG GGT GGA CAC ACC TTC GGA AAA ACC CAT GTT  840
 261 Asn Asp Glu Glu Thr Val Ala Leu Ile Ala Gly Gly His Thr Phe Gly Lys Thr His Gly  280

841 GCT GCC GAT GCG GAG AAA TAT GTG GGC GGA GAG CCT GCC GCA GGT ATT GAA GAA ATG  900
 281 Ala Ala Asp Ala Glu Lys Tyr Val Gly Arg Glu Pro Ala Ala Gly Ile Glu Glu Met  300

901 AGC CTG GGG TGG AAA AAC TAC GGC ACC GGT GAT ACC ATC ACC AGT GGA  960
 321 Ser Leu Gly Trp Lys Asn Thr Tyr Gly Thr Gly Asp Ala Asp Thr Ile Thr Ser Gly  320

961 CTA GAA GGC GCC TGG GCC ACC CCT ACT CAA TGG AGC AAT AAC TTT TTT GAA AAC CTC 1020
 321 Leu Glu Gly Ala Trp Ala Thr Pro Thr Gln Trp Ser Asn Asn Phe Phe Glu Asn Leu  340

1021 TTT GGT TAC GAG TGG GAG CTT ACC AAA AGT CCA GCT CCA GGA GCT TAT CAG TGG AAA CCA AAA 1080
 341 Phe Gly Tyr Glu Trp Glu Leu Thr Lys Ser Pro Ala Gly Ala Tyr Gln Trp Lys Pro Lys  360

1081 GAC GGT GCC GGG GCT GGC ACC ATA CCG GAT GCA CAT GAT CCC AGC AAG TCG CAC GCT CCA 1140
 361 Asp Gly Ala Gly Ala Gly Thr Ile Pro Asp Ala His Asp Pro Ser Lys Ser His Ala Pro  380

1141 TTT ATG CTC ACT ACG GAC CTG GCG CTG CGC ATG GAC CCT GAT TAC GAA AAA ATT TCT CGA 1200
 381 Phe Met Leu Thr Thr Asp Leu Ala Leu Arg Met Asp Pro Asp Tyr Glu Lys Ile Ser Arg  400

1201 CGG TAC TAT GAA AAC CCT GAT GAG TTT GCA GAT GCT TTC TTC GCA AAA GCA TGG TAC AAA CTG 1260
 401 Arg Tyr Tyr Glu Asn Pro Asp Glu Phe Ala Asp Ala Phe Ala Lys Ala Trp Tyr Lys Leu  420

1261 ACA CAC AGA GAT ATG GGA GAC TAC CGC AAG GTG CCA GAA GTG CCT CAG GAA GAC 1320
 421 Thr His Arg Asp Met Gly Asp Tyr Arg Lys Val Pro Glu Val Pro Gln Glu Asp  440

1321 CTC ATC TGG CAA GAC CTA AGC CAT GTA GAC CCT CTT GTA GAC GAA AAC GAT ATT 1380
 441 Leu Ile Trp Gln Asp Val Ser His Val Asp Pro Leu Val Asp Glu Asn Asp Ile  460
```

FIG. 2C

```
1381 GAA GGC CTA AAA GCC AAA ATC CTG GAA TCG GGA CTG ACG GTA AGC GAG CTG GTA AGC ACG 1440
 461 Glu Gly Leu Lys Ala Lys Ile Leu Glu Ser Gly Leu Thr Val Ser Glu Leu Val Ser Thr  480

1441 GCA TGG GCT TCT GCA TCT ACT TTT AGA AAC TCT GAC AAG CGC GGT GCC AAC GGT GCA 1500
 481 Ala Trp Ala Ser Ala Ser Thr Phe Arg Asn Ser Asp Lys Arg Gly Ala Asn Gly Ala  500

1501 CGT ATA CGA CTG GCC CCA CAA CTG GCC GAA TGG GAA GTA AAC CCT CAG CAA CTT GCC AGG 1560
 501 Arg Ile Arg Leu Ala Pro Gln Leu Ala Glu Trp Glu Val Asn Pro Gln Gln Leu Ala Arg  520

1561 GTA CTC AAA ACA CTA GAA GGT ATC CAG ATT AAC CAG CAA TCA GAT AAC AAA 1620
 521 Val Leu Lys Thr Leu Glu Gly Ile Gln Ile Asn Gln Gln Ser Asp Asn Lys  540

1621 GCA GTA TCG TTG GCC CTG ATT GTG CTG GGC TGT GCC GGT GTA GAA AAA GCT GCA 1680
 541 Ala Val Ser Leu Ala Leu Ile Val Leu Ala Gly Cys Ala Gly Val Glu Lys Ala Ala  560

1681 AAA GAT GCT GGC CAT GAG GTG CAG GTG CCT GTC AAC CCG GGA CGA GCG GAT GCC ACC GCT 1740
 561 Lys Asp Ala Gly His Glu Val Gln Val Pro Phe Asn Pro Gly Arg Ala Asp Ala Thr Ala  580

1741 GAG CAA ACC GAT GTG GAA GCT AAA GTA TTC GAA GCA CTA GAG CTG GCT GAC GGC TTT AGA AAC 1800
 581 Glu Gln Thr Asp Val Glu Ala Lys Val Phe Glu Ala Leu Glu Leu Ala Asp Gly Phe Arg Asn  600

1801 TAC ATT AAA CCG GAG CAT AAA GTA TCC GCT GAG GAA ATG CTC GTA GAC CGG GCG CAG CTT 1860
 601 Tyr Ile Lys Pro Glu His Lys Val Ser Ala Glu Glu Met Leu Val Asp Arg Ala Gln Leu  620

1861 CTG TCG CTT TCG GCA CCA GAA ATG ACT GCT TTG GTA CTA CTT GGC ATG CGT GTA CTG GGC ACC 1920
 621 Leu Ser Leu Ser Ala Pro Glu Met Thr Ala Leu Val Leu Leu Gly Met Arg Val Leu Gly Thr  640

1921 AAC TAC GAC GGT TCG CAG CAT TCG CAG GTG TTT ACA AAT AAG CCG GGT CAG CTA TCC AAT GAC 1980
 641 Asn Tyr Asp Gly Ser Gln His Ser Gln Val Phe Thr Asn Lys Pro Gly Gln Leu Ser Asn Asp  660

1981 TTC TTT GTA GAC CTC AAC CTC TAC AAC ACT AAA TGG CGA GCC AGC GAT GAA TCA GAC AAA 2040
 661 Phe Phe Val Asp Leu Asn Leu Tyr Asn Thr Lys Trp Arg Ala Ser Asp Glu Ser Asp Lys  680

2041 GTT TTT GAA GGC AGA GAC TTC AAA ACT GGC AGT AAG TGG AGT GGC ACC CGG GTA GAC 2100
 681 Val Phe Glu Gly Arg Asp Phe Lys Thr Gly Ser Lys Trp Ser Gly Thr Arg Val Asp  700
```

FIG. 2D

```
2101 CTG ATC TTC GGA TCC AAT TCC GAG CTA AGA GCC CTC GCA GAA GTG TAC GGC TGT GCA GAT 2160
 701 Leu Ile Phe Gly Ser Asn Ser Glu Leu Arg Ala Leu Ala Glu Val Tyr Gly Cys Ala Asp  720

2161 TCT GAA GAA AAG TTT GTT AAA GAT TTT AAA GAT GCC TGG GCC AAA GTA ATG GAC CTG GAC 2220
 721 Ser Glu Glu Lys Phe Val Lys Asp Phe Lys Asp Ala Trp Ala Lys Val Met Asp Leu Asp  740

2221 CGG TTT GAT CTG AAA TAA 2238
 741 Arg Phe Asp Leu Lys End  746
```

CATALASES

This is a divisional of copending application Ser. No. 08/674,887, filed Jul. 3, 1996.

This invention relates to newly identified polynucleotides, polypeptides encoded by such polynucleotides, the use of such polynucleotides and polypeptides, as well as the production and isolation of such polynucleotides and polypeptides. More particularly, the polynucleotides and polypeptides of the present invention have been putatively identified as catalases.

Generally, in processes where hydrogen peroxide is a by-product, catalases can be used to destroy or detect hydrogen peroxide, e.g., in production of glyoxylic acid and in glucose sensors. Also, in processes where hydrogen peroxide is used as a bleaching or antibacterial agent, catalases can be used to destroy residual hydrogen peroxide, e.g. in contact lens cleaning, in bleaching steps in pulp and paper preparation and in the pasteurization of dairy products. Further, such catalases can be used as catalysts for oxidation reactions, e.g., epoxidation and hydroxylation.

In accordance with one aspect of the present invention, there are provided novel enzymes, as well as active fragments, analogs and derivatives thereof.

In accordance with another aspect of the present invention, there are provided isolated nucleic acid molecules encoding the enzymes of the present invention including mRNAs, cDNAs, genomic DNAs as well as active analogs and fragments of such enzymes.

In accordance with yet a further aspect of the present invention, there is provided a process for producing such polypeptides by recombinant techniques comprising culturing recombinant prokaryotic and/or eukaryotic host cells, containing a nucleic acid sequence of the present invention, under conditions promoting expression of said enzymes and subsequent recovery of said enzymes In accordance with yet a further aspect of the present invention, there are also provided nucleic acid probes comprising nucleic acid molecules of sufficient length to specifically hybridize to a nucleic acid sequence of the present invention.

In accordance with yet a further aspect of the present invention, there is provided a process for utilizing such enzymes, or polynucleotides encoding such enzymes, for in vitro purposes related to scientific research, for example, to generate probes for identifying similar sequences which might encode similar enzymes from other organisms by using certain regions, i.e., conserved sequence regions, of the nucleotide sequence.

In accordance with yet a further aspect of the present invention, there is provided antibodies to such catalases. These antibodies are as probes to screen libraries from these or other organisms for members of the libraries which could have the same catalase activity or a cross reactive activity.

These and other aspects of the present invention should be apparent to those skilled in the art from the teachings herein.

BRIEF DESCRIPTION OF THE DRAWINGS

The following drawings are illustrative of an embodiment of the invention and are not meant to limit the scope of the invention as encompassed by the claims.

FIG. 1 shows the full-length DNA sequence (SEQ ID NO: 5) and the corresponding deduced amino acid sequence (SEQ ID NO: 6) for *Alcaligenes* (*Deleya*) *aquamarinus* Catalase-64CA2.

FIG. 2 shows the full-length DNA sequence (SEQ ID NO: 7) and the corresponding deduced amino acid sequence (SEQ ID NO: 8) for *Microscilla furvescens* Catalase 53CA1.

DETAILED DESCRIPTION OF PREFERRED EMBODIMENTS

In order to facilitate understanding of the following description and examples which follow certain frequently occurring methods and/or terms will be described.

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. For example, with respect to polynucleotides, the term isolated means that it is separated from the nucleic acid and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such polynucleotides still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y. (1989).

The term "gene" means the segment of DNA involved in 4producing a polypeptide chain; it includes regions preceding and following the coding region (leader and trailer) as well as intervening sequences (introns) between individual coding segments (exons).

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequences ultimately process to produce the desired protein.

"Recombinant" enzymes refer to enzymes produced by recombinant DNA techniques; i.e., produced from cells transformed by an exogenous DNA construct encoding the desired enzyme. "Synthetic" enzymes are those prepared by chemical synthesis.

A DNA "coding sequence of" or a "nucleotide sequence encoding" a particular enzyme, is a DNA sequence which is transcribed and translated into an enzyme when placed under the control of appropriate regulatory sequences.

"Plasmids" are designated by a lower case "p" preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel et al., *Nucleic Acids Res.,* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in Sambrook and Maniatis, Molecular Cloning: A Laboratory Manual, Cold Spring Harbor Laboratory, 1989.

In accordance with an aspect of the present invention, there are provided isolated nucleic acids (polynucleotides) which encode for the mature enzyme having the deduced amino acid sequence of FIG. 1 (SEQ ID NO: 6).

In accordance with another aspect of the present invention, there are provided isolated nucleic acids (polynucleotides) which encode for the mature enzyme having the deduced amino acid sequence of FIG. 2 (SEQ ID NO: 8).

The polynucleotides of this invention were originally recovered from a genomic gene library derived from two sources. The first, *Alcaligenes* (*Delaya*) *aquamarinus,* is a β-Proteobacteria. It is a gram-negative rod that grows optimally at 26° C. and pH 7.2. The second, *Microscilla furvescens,* is a Cytophagales (Bacteria) isolated from Samoa. It is a gram-negative rod with gliding motility that grows optimally at 30° C. and pH 7.0.

With respect to *Alcaligenes* (*Delaya*) *aquamarinus,* the protein with the closest amino acid sequence identity of which the inventors are currently aware is the *Microscilla furvescens* catalase (59.5% protein identity; 60% DNA identity). The next closest is a *Mycobacterium tuberculosis* catalase (KatG), with a 54% protein identity.

With respect to *Microscilla furvescens,* the protein with the closest amino acid sequence identity of which the inventors are currently aware is catalase I of *Bacillus stearothermophilus,* which has a 69% amino acid identity.

Accordingly, the polynucleotides and enzymes encoded thereby are identified by the organism from which they were isolated. Such are sometimes referred to below as "64CA2" (FIG. 1 and SEQ ID NOS: 5 and 6) and "53CA1" (FIG. 2 and SEQ ID NOS: 7 and 8).

One means for isolating the nucleic acid molecules encoding the enzymes of the present invention is to probe a gene library with a natural or artificially designed probe using art recognized procedures (see, for example: Current Protocols in Molecular Biology, Ausubel F. M. et al. (EDS.) Green Publishing Company Assoc. and John Wiley Interscience, New York, 1989, 1992). It is appreciated by one skilled in the art that the polynucleotides of SEQ ID NOS: 5 and 7, or fragments thereof (comprising at least 12 contiguous nucleotides), are particularly useful probes. Other particularly useful probes for this purpose are hybridizable fragments of the sequences of SEQ ID NOS: 5 and 7 (i.e., comprising at least 12 contiguous nucleotides).

With respect to nucleic acid sequences which hybridize to specific nucleic acid sequences disclosed herein, hybridization may be carried out under conditions of reduced stringency, medium stringency or even stringent conditions. As an example of oligonucleotide hybridization, a polymer membrane containing immobilized denatured nucleic acids is first prehybridized for 30 minutes at 45° C. in a solution consisting of 0.9 M NaCl, 50 mM $NaH_2PO_4$, pH 7.0, 5.0 mM $Na_2EDTA$, 0.5% SDS, 10× Denhardt's, and 0.5 mg/mL polyriboadenylic acid. Approximately $2×10^7$ cpm (specific activity $4-9×10^8$ cpm/ug) of $^{32}P$ end-labeled oligonucleotide probe are then added to the solution. After 12–16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at (Tm less 10° C.) for the oligonucleotide probe. The membrane is then exposed to auto-radiographic film for detection of hybridization signals.

Stringent conditions means hybridization will occur only if there is at least 90% identity, preferably at least 95% identity and most preferably at least 97% identity between the sequences. Further, it is understood that a section of a 100 bps sequence that is 95 bps in length has 95% identity with the 1090 bps sequence from which it is obtained. See J. Sambrook et al., *Molecular Cloning, A Laboratory Manual, 2d Ed.,* Cold Spring Harbor Laboratory (1989) which is hereby incorporated by reference in its entirety. Also, it is understood that a fragment of a 100 bps sequence that is 95 bps in length has 95% identity with the 100 bps sequence from which it is obtained.

As used herein, a first DNA (RNA) sequence is at least 70% and preferably at least 80% identical to another DNA (RNA) sequence if there is at least 70% and preferably at least a 80% or 90% identity, respectively, between the bases of the first sequence and the bases of the another sequence, when properly aligned with each other, for example when aligned by BLASTN.

The present invention relates to polynucleotides which differ from the reference polynucleotide such that the differences are silent, for example, the amino acid sequence encoded by the polynucleotides is the same. The present invention also relates to nucleotide changes which result in amino acid substitutions, additions, deletions, fusions and truncations in the polypeptide encoded by the reference polynucleotide. In a preferred aspect of the invention these polypeptides retain the same biological action as the polypeptide encoded by the reference polynucleotide.

The polynucleotides of this invention were recovered from genomic gene libraries from the organisms identified above. Gene libraries were generated from a Lambda ZAP II cloning vector (Stratagene Cloning Systems). Mass excisions were performed on these libraries to generate libraries in the pBluescript phagemid. Libraries were generated and excisions were performed according to the protocols/methods hereinafter described.

The polynucleotides of the present invention may be in the form of RNA or DNA, which DNA includes cDNA, genomic DNA, and synthetic DNA. The DNA may be double-stranded or single-stranded, and if single stranded may be coding strand or non-coding (anti-sense) strand. The coding sequences which encodes the mature enzymes may be identical to the coding sequences shown in FIGS. 1–2 (SEQ ID NOS: 5 & 7) or may be a different coding sequence which coding sequence, as a result of the redundancy or degeneracy of the genetic code, encodes the same mature enzymes as the DNA of FIGS. 1–2 (SEQ ID NOS: 6 & 8).

The polynucleotide which encodes for the mature enzyme of FIGS. 1–2 (SEQ ID NOS: 6 & 8) may include, but is not limited to: only the coding sequence for the mature enzyme; the coding sequence for the mature enzyme and additional coding sequence such as a leader sequence or a proprotein sequence; the coding sequence for the mature enzyme (and optionally additional coding sequence) and non-coding sequence, such as introns or non-coding sequence 5' and/or 3' of the coding sequence for the mature enzyme.

Thus, the term "polynucleotide encoding an enzyme (protein)" encompasses a polynucleotide which includes only coding sequence for the enzyme as well as a polynucleotide which includes additional coding and/or non-coding sequence.

The present invention further relates to variants of the hereinabove described polynucleotides which encode for fragments, analogs and derivatives of the enzymes having the deduced amino acid sequences of FIGS. 1–2 (SEQ ID NOS: 6 & 8). The variant of the polynucleotide may be a naturally occurring allelic variant of the polynucleotide or a non-naturally occurring variant of the polynucleotide.

Thus, the present invention includes polynucleotides encoding the same mature enzymes as shown in FIGS. 1–2 (SEQ ID NOS: 6 & 8) as well as variants of such polynucleotides which variants encode for a fragment, derivative or analog of the enzymes of FIGS. 1–2 (SEQ ID NOS: 6 & 8). Such nucleotide variants include deletion variants, substitution variants and addition or insertion variants.

As hereinabove indicated, the polynucleotides may have a coding sequence which is a naturally occurring allelic variant of the coding sequence shown in FIGS. 1–2 (SEQ ID NOS: 5 & 7). As known in the art, an allelic variant is an alternate form of a polynucleotide sequence which may have a substitution, deletion or addition of one or more nucleotides, which does not substantially alter the function of the encoded enzyme. Also, using directed and other evolution strategies, one may make very minor changes in DNA sequence which can result in major changes in function.

Fragments of the full length gene of the present invention may be used as hybridization probes for a cDNA or a genomic library to isolate the full length DNA and to isolate other DNAs which have a high sequence similarity to the gene or similar biological activity. Probes of this type preferably have at least 10, preferably at least 15, and even more preferably at least 30 bases and may contain, for example, at least 50 or more bases. In fact, probes of this type having at least up to 150 bases or greater may be preferably utilized. The probe may also be used to identify a DNA clone corresponding to a full length transcript and a genomic clone or clones that contain the complete gene including regulatory and promotor regions, exons and introns. An example of a screen comprises isolating the coding region of the gene by using the known DNA sequence to synthesize an oligonucleotide probe. Labeled oligonucleotides having a sequence complementary or identical to that of the gene or portion of the gene sequences of the present invention are used to screen a library of genomic DNA to determine which members of the library the probe hybridizes to.

It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. The probes are thus useful to isolate complementary copies of DNA from other sources or to screen such sources for related sequences.

The present invention further relates to polynucleotides which hybridize to the hereinabove-described sequences if there is at least 70%, preferably at least 90%, and more preferably at least 95% identity between the sequences. (As indicated above, 70% identity would include within such definition a 70 bps fragment taken from a 100 bp polynucleotide, for example.) The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode enzymes which either retain substantially the same biological function or activity as the mature enzyme encoded by the DNA of FIGS. 1–2 (SEQ ID NOS: 5 & 7). In referring to identity in the case of hybridization, as known in the art, such identity refers to the complementarity of two polynucleotide segments.

Alternatively, the polynucleotide may have at least 15 bases, preferably at least 30 bases, and more preferably at least 50 bases which hybridize to any part of a polynucleotide of the present invention and which has an identity thereto, as hereinabove described, and which may or may not retain activity. For example, such polynucleotides may be employed as probes for the polynucleotides of SEQ ID NOS: 5 & 7, for example, for recovery of the polynucleotide or as a diagnostic probe or as a PCR primer.

Thus, the present invention is directed to polynucleotides having at least a 70% identity, preferably at least 90% identity and more preferably at least a 95% identity to a polynucleotide which encodes the enzymes of SEQ ID NOS: 6 & 8 as well as fragments thereof, which fragments have at least 15 bases, preferably at least 30 bases, more preferably at least 50 bases and most preferably fragments having up to at least 150 bases or greater, which fragments are at least 90% identical, preferably at least 95% identical and most preferably at least 97% identical to any portion of a polynucleotide of the present invention.

The terms "fragment," "derivative" and "analog" when referring to the enzymes of FIGS. 1–2 (SEQ NOS. 6 & 8)

means enzymes which retain essentially the same biological function or activity as such enzymes. Thus, an analog includes a proprotein which can be activated by cleavage of the proprotein portion to produce an active mature enzyme.

The enzymes of the present invention may be a recombinant enzyme, a natural enzyme or a synthetic enzyme, preferably a recombinant enzyme.

The fragment, derivative or analog of the enzymes of FIGS. 1–2 (SEQ ID NOS: 6 & 8) may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature enzyme is fused with another compound, such as a compound to increase the half-life of the enzyme (for example, polyethylene glycol), or (iv) one in which the additional amino acids are fused to the mature enzyme, such as a leader or secretory sequence or a sequence which is employed for purification of the mature enzyme or a proprotein sequence. Such fragments, derivatives and analogs are deemed to be within the scope of those skilled in the art from the teachings herein.

The enzymes and polynucleotides of the present invention are preferably provided in an isolated form, and preferably are purified to homogeneity.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which may be, for example, a cloning vector such as an expression vector. The vector may be, for example, in the form of a plasmid, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing enzymes by recombinant techniques. Thus, for example, the polynucleotide may be included in any one of a variety of expression vectors for expressing an enzyme. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Bacillus subtilis; fungal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example; Bacterial: pQE70, pQE60, pQE-9 (Qiagen), pBluescript II KS(Stratagene), ptrc99a, pKK223-3, pDR540, pRIT2T (Pharmacia); Eukaryotic: pXT1, pSG5 (Stratagene) pSVK3, pBPV, pMSG, pSVL SV40 (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., *Basic Methods in Molecular Biology*, (1986)).

The constructs in host cells can be used in a conventional manner to produce the gene product encoded by the recombinant sequence. Alternatively, the enzymes of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al., *Molecular Cloning: A Laboratory Manual, Second Edition*, Cold Spring Harbor, N.Y., (1989), the disclosure of which is hereby incorporated by reference.

Transcription of the DNA encoding the enzymes of the present invention by higher eukaryotes is increased by inserting an enhancer sequence into the vector. Enhancers are cis-acting elements of DNA, usually about from 10 to 300 bp that act on a promoter to increase its transcription. Examples include the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated enzyme. Optionally, the heterologous sequence can encode a fusion enzyme including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The enzyme can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention may be glycosylated or may be non-glycosylated. Enzymes of the invention may or may not also include an initial methionine amino acid residue.

Antibodies generated against the enzymes corresponding to a sequence of the present invention can be obtained by direct injection of the enzymes into an animal or by administering the enzymes to an animal, preferably a nonhuman. The antibody so obtained will then bind the enzymes itself. In this manner, even a sequence encoding only a fragment of the enzymes can be used to generate antibodies binding the whole native enzymes. Such antibodies can then be used to isolate the enzyme from cells expressing that enzyme.

For preparation of monoclonal antibodies, any technique which provides antibodies produced by continuous cell line cultures can be used. Examples include the hybridoma technique (Kohler and Milstein, *Nature*, 256:495–497, 1975), the trioma technique, the human B-cell hybridoma technique (Kozbor et al., *Immunology Today* 4:72, 1983), and the EBV-hybridoma technique to produce human monoclonal antibodies (Cole et al., in *Monoclonal Antibodies and Cancer Therapy*, Alan R. Liss, Inc., pp. 77–96, 1985).

Techniques described for the production of single chain antibodies (U.S. Pat. No. 4,946,778) can be adapted to produce single chain antibodies to immunogenic enzyme products of this invention. Also, transgenic mice may be used to express humanized antibodies to immunogenic enzyme products of this invention.

Antibodies generated against an enzyme of the present invention may be used in screening for similar enzymes from other organisms and samples. Such screening techniques are known in the art, for example, one such screening assay is described in Sambrook and Maniatis, Molecular Cloning: A Laboratory Manual (2d Ed.), vol. 2:Section 8.49, Cold Spring Harbor Laboratory, 1989, which is hereby incorporated by reference in its entirety.

The present invention will be further described with reference to the following examples; however, it is to be understood that the present invention is not limited to such examples. All parts or amounts, unless otherwise specified, are by weight.

EXAMPLE 1

Production of the Expression Gene Bank

An *E. coli* catalase negative host strain CAT500 was infected with a phage solution containing sheared pieces of DNA from *Alcaligenes* (*Deleya*) *aquamarinus* in pBluescript plasmid and plated on agar containing LB with ampicillin (100 μg/mL), methicillin (80 μg/mL) and kanamycin (100 μg/mL) according to the method of Hay and Short (Hay, B. and Short, J., *J. Strategies,* 5:16, 1992). The resulting colonies were picked with sterile toothpicks and used to singly inoculate each of the wells of 96-well microtiter plates. The wells contained 250 μL of SOB media with 100 μg/mL ampicillin, 80 μg/mL methicillin, and (SOB Amp/Meth/Kan). The cells were grown overnight at 37° C. without shaking. This constituted generation of the "Source-GeneBank"; each well of the Source GeneBank thus contained a stock culture of *E. coli* cells, each of which contained a pBluescript plasmid with a unique DNA insert. Same protocol was adapted for screening catalase from *Microscilla furvescens*.

EXAMPLE 2

Screening for Catalase Activity

The plates of the Source GeneBank were used to multiply inoculate a single plate (the "Condensed Plate") containing in each well 200 μL of SOB Amp/Meth/Kan. This step was performed using the High Density Replicating Tool (HDRT) of the Beckman Biomek with a 1% bleach, water, isopropanol, air-dry sterilization cycle in between each inoculation. Each well of the Condensed Plate thus contained 4 different pBluescript clones from each of the source library plates. Nine such condensed plates were prepared and grown for 16h at 37° C.

One hundred (100) μL of the overnight culture was transferred to the white polyfiltronic assay plates containing 100 μL Hepes/well. A 0.03% solution of hydrogen peroxide was made in 5% Triton and 20 μL of this solution was added to each well. The plates were incubated at room temperature for one hour. After an hour, 50 μL of 120 mM 3-(p-hydroxyphenyl)-propionic acid and 1 unit of horseradish peroxidase were added to each well and the plates were incubated at room temperature for 1 hour. To quench the reaction, 50 μL of 1 M Tris-base was added to each well. The wells were excited on a fluorometer at 320 nm and read at 404 nm. A low value signified a positive catalase hit.

EXAMPLE 3

Isolation and Purification of the Active Clone

In order to isolate the individual clone which carried the activity, the Source GeneBank plates were thawed and the individual wells used to singly inoculate a new plate containing SOB Amp/Meth/Kan. As above the plate was incubated at 37° C. to grow the cells, and assayed for activity as described above. Once the active well from the source plate was identified, the cells from the source plate were streaked on agar with LB/Amp/Meth/Kan and grown overnight at 37° C. to obtain single colonies. Eight single colonies were picked with a sterile toothpick and used to singly inoculate the wells of a 96-well microtiter plate. The wells contained 250 μL of SOB Amp/Meth/Kan. The cells were grown overnight at 37° C. without shaking. A 100 μL aliquot was removed from each well and assayed as indicated above. The most active clone was identified and the remaining 150 μL of culture was used to streak an agar plate with LB/Amp/Meth/Kan. Eight single colonies were picked, grown and assayed as above. The most active clone was used to inoculate 3 mL cultures of LB/Amp/Meth/Kan, which were grown overnight. The plasmid DNA was isolated from the cultures and utilized for sequencing.

EXAMPLE 4

Expression of Catalases

DNA encoding the enzymes of the present invention, SEQ ID NOS: 7 and 9, were initially amplified from a pBluescript vector containing the DNA by the PCR technique using the primers noted herein. The amplified sequences were then inserted into the respective pQE vector listed beneath the primer sequences, and the enzyme was expressed according to the protocols set forth herein. The 5' and 3' oligonucleotide primer sequences used for subcloning and vectors for the respective genes are as follows:

Alcaligenes (Deleya aquamarinus catalse: (pQET vector)

```
5' Primer   CCGAGAATTCATTAAAGAGGAGAAATTAACTATGAATAACGCATCCGCTGAC   EcoRI   (SEQ ID NO:1)

3' Primer   CGGAAAGCTTTTACGACGCGACGTCGAAACG   HindIII   (SEQ ID NO:2)
```

Microscilla furvescens catalase: (pQET vector)

```
5' Primer   CCGAGAATTCATTAAAGAGGAGAAATTAACTATGGAAAATCACAAACACTCA   EcoRI   (SEQ ID NO:3)

3' Primer   CGAAGGTACCTTATTTCAGATCAAACCGGTC   KpnI   (SEQ ID NO:4)
```

The restriction enzyme sites indicated correspond to the restriction enzyme sites on the bacterial expression vector indicated for the respective gene (Qiagen, Inc. Chatsworth, Calif.). The pQET vector encodes antibiotic resistance (Amp$^r$), a bacterial origin of replication (ori), an IPTG-regulatable promoter operator (P/O), a ribosome binding site (RBS), a 6-His tag and restriction enzyme sites.

The pQET vector was digested with the restriction enzymes indicated. The amplified sequences were ligated into the respective pQET vector and inserted in frame with the sequence encoding for the RBS. The native stop codon was incorporated so the genes were not fused to the His tag of the vector. The ligation mixture was then used to transform the E. coli strain UM255/pREP4 (Qiagen, Inc.) by electroporation. UM255/pREP4 contains multiple copies of the plasmid pREP4, which expresses the lad repressor and also confers kanamycin resistance (Kan$^r$). Transformants were identified by their ability to grow on LB plates and ampicillin/kanamycin resistant colonies were selected. Plasmid DNA was isolated and confirmed by restriction analysis. Clones containing the desired constructs were grown overnight (O/N) in liquid culture in LB media supplemented with both Amp (100 ug/ml) and Kan (25 ug/ml). The O/N culture was used to inoculate a large culture at a ratio of 1:100 to 1:250. The cells were grown to an optical density 600 (O.D.$^{600}$) of between 0.4 and 0.6. IPTG ("Isopropyl-B-D-thiogalacto pyranoside") was then added to a final concentration of 1 mM. IPTG induces by inactivating the lad repressor, clearing the P/O leading to increased gene expression. Cells were grown an extra 3 to 4 hours. Cells were then harvested by centrifugation. The primer sequences set out above may also be employed to isolate the target gene from the deposited material by hybridization techniques described above.

CITED LITERATURE

1) U.S. Pat. No. 5,439,813, Aug. 8, 1995, Production of glyoxylic acid with glycolate oxidase and catalase immobilized on oxirane acrylic beads, Anton, D. L., Wilmington, Del., DiCosimo, R., Wilmington, Del., Gavagan, J. E., Wilmington, Del.
2) U.S. Pat. No. 5,360,732, Nov. 1, 1994, Production of Aspergillus niger catalase-R, Berka, R. M., San Mateo, Calif., Fowler, T., Redwood City, Calif., Rey, M. W., San Mateo, Calif.
3) U.S. Pat. No. 4,460,686, Jul. 17, 1984, Glucose oxidation with immobilized glucose oxidase-catalase, Hartmeier, W., Ingelheim am Rhein, Germany
4) U.S. Pat. No. 5,447,650, Sep. 5, 1995, Composition for preventing the accumulation of inorganic deposits on contact lenses, Cafaro, D. P., Santa Ana, Calif.
5) U.S. Pat. No. 5,362,647, Nov. 8, 1994, Compositions and methods for destroying hydrogen peroxide, Cook, J. N., Mission Viejo, Calif., Worsley, J. L., Irvine, Calif.
6) U.S. Pat. No. 5,266,338, 1993, Cascione, A. S., Rapp, H.
7) Patrick Dhaese, "Catalase: An Enzyme with Growing Industrial Potential" CHIMICA OGGIA/Chemistry Today, January/February, 1996.

What is claimed is:

1. An isolated enzyme having an amino acid sequence as set forth in SEQ ID NO:6.

2. An isolated enzyme having an amino acid sequence as set forth in SEQ ID NO:8.

* * * * *

UNITED STATES PATENT AND TRADEMARK OFFICE
CERTIFICATE OF CORRECTION

PATENT NO. : 6,074,860
DATED : 6/13/2000
INVENTOR(S) : Robertson et al.

It is certified that error appears in the above-identified patent and that said Letters Patent is hereby corrected as shown below:

Column 1, line 61, change "Figure 1 shows" to --Figures 1A-1D show--.

Column 1, line 65, change "Figures 2 shows" to --Figures 2A-2D show--.

Signed and Sealed this

First Day of August, 2000

Q. TODD DICKINSON

*Attest:*

*Attesting Officer*  *Director of Patents and Trademarks*

UNITED STATES PATENT AND TRADEMARK OFFICE
CERTIFICATE OF CORRECTION

PATENT NO.   : 6,074,860
DATED        : June 13, 2000
INVENTOR(S)  : Robertson et al.

It is certified that error appears in the above-identified patent and that said Letters Patent is hereby corrected as shown below:

<u>Title page,</u>
Item [75], Inventors, replace "Adhikary; Robert S." with -- Adhikari; Robert S. --

Signed and Sealed this

Fourteenth Day of January, 2003

JAMES E. ROGAN
*Director of the United States Patent and Trademark Office*

```
                       SEQUENCE LISTING (1) GENERAL INFORMATION:

(iii) NUMBER OF SEQUENCES:   8

(2) INFORMATION FOR SEQ ID NO:1:

(i) SEQUENCE CHARACTERISTICS:
          (A) LENGTH:   52 NUCLEOTIDES (B) TYPE:   NUCLEIC ACID (C) STRANDEDNESS:   SINGLE (D) TOPOLOGY:   LINEAR (ii) MOLECULE TYPE:   DNA (xi) SEQUENCE DESCRIPTION:   SEQ ID NO:1:

CCGAGAATTC ATTAAAGAGG AGAAATTAAC TATGAATAAC GCATCCGCTG AC          52

(2) INFORMATION FOR SEQ ID NO:2:

(i) SEQUENCE CHARACTERISTICS:
          (A) LENGTH:   31 NUCLEIC ACID (B) TYPE:   NUCLEIC ACID (C) STRANDEDNESS:   SINGLE (D) TOPOLOGY:   LINEAR (ii) MOLECULE TYPE:   DNA (xi) SEQUENCE DESCRIPTION:   SEQ ID NO:2:
```

```
CGGAAAGCTT TTACGACGCG ACGTCGAAAC G                                    31

(2) INFORMATION FOR SEQ ID NO:3:

(i) SEQUENCE CHARACTERISTICS:
        (A) LENGTH:  52 NUCLEOTIDES (B) TYPE:  NUCLEIC ACID (C) STRANDEDNESS:  SINGLE (D) TOPOLOGY:  LINEAR (ii) MOLECULE TYPE:  DNA (xi) SEQUENCE DESCRIPTION:  SEQ ID NO:3:

CCGAGAATTC ATTAAAGAGG AGAAATTAAC TATGGAAAAT CACAAACACT CA             52

(2) INFORMATION FOR SEQ ID NO:4:

(i) SEQUENCE CHARACTERISTICS:
        (A) LENGTH:  31 NUCLEOTIDES (B) TYPE:  NUCLEIC ACID (C) STRANDEDNESS:  SINGLE (D) TOPOLOGY:  LINEAR (ii) MOLECULE TYPE:  DNA (xi) SEQUENCE DESCRIPTION:  SEQ ID NO:4:

CGAAGGTACC TTATTTCAGA TCAAACCGGT C                                    31

(2) INFORMATION FOR SEQ ID NO:5:

(i) SEQUENCE CHARACTERISTICS:
        (A) LENGTH:  2262 NUCLEOTIDES (B) TYPE:  NUCLEIC ACID (C) STRANDEDNESS:  SINGLE (D) TOPOLOGY:  LINEAR (ii) MOLECULE TYPE:  Oligonucleotide (xi) SEQUENCE DESCRIPTION:  SEQ ID NO:5:

ATG AAT AAC GCA TCC GCT GAC GAT CTA CAC AGT AGC TTG CAG CAA AGA       48
Met Asn Asn Ala Ser Ala Asp Asp Leu His Ser Ser Leu Gln Gln Arg
                 5                  10                  15

TGC AGA GCA TTT GTT CCC TTG GTA TCG CCA AGG CAT AGA GCA ATA AGG       96
Cys Arg Ala Phe Val Pro Leu Val Ser Pro Arg His Arg Ala Ile Arg
             20                  25                  30

GAG AGA GCT ATG AGC GGT AAA TGT CCT GTC ATG CAC GGT GGT AAC ACC      144
Glu Arg Ala Met Ser Gly Lys Cys Pro Val Met His Gly Gly Asn Thr
         35                  40                  45

TCG ACC GGT ACT TCC AAC AAA GAT TGG TGG CCG GAA GGG TTG AAC CTG      192
Ser Thr Gly Thr Ser Asn Lys Asp Trp Trp Pro Glu Gly Leu Asn Leu
     50                  55                  60

GAT ATT TTG CAT CAG CAA GAT CGC AAA TCA GAC CCG ATG GAT CCG GAT      240
Asp Ile Leu His Gln Gln Asp Arg Lys Ser Asp Pro Met Asp Pro Asp
65                  70                  75                  80

TTC AAC TAC CGT GAA GAA GTA CGC AAG CTC GAT TTC GAC GCG CTG AAG      288
```

```
                Phe Asn Tyr Arg Glu Glu Val Arg Lys Leu Asp Phe Asp Ala Leu Lys
                                85                  90                  95

AAA GAT GTC CAC GCG TTG ATG ACC GAT AGC CAA GAG TGG TGG CCC GCT              336
Lys Asp Val His Ala Leu Met Thr Asp Ser Gln Glu Trp Trp Pro Ala
            100                 105                 110

GAC TGG GGG CAC TAC GGC GGT TTG ATG ATC CGT ATG GCT TGG CAC TCC              384
Asp Trp Gly His Tyr Gly Gly Leu Met Ile Arg Met Ala Trp His Ser
        115                 120                 125

GCT GGC ACC TAC CGT ATT GCT GAT GGC CGT GGG GGC GGT GGT ACC GGA              432
Ala Gly Thr Tyr Arg Ile Ala Asp Gly Arg Gly Gly Gly Thr Gly
130                 135                 140

AGC CAG CGC TTT GCA CCG CTC AAC TCC TGG CCG GAC AAC GTC AGC CTG              480
Ser Gln Arg Phe Ala Pro Leu Asn Ser Trp Pro Asp Asn Val Ser Leu
145                 150                 155                 160

GAT AAA GCG CGC CGT CTG CTG TGG CCG ATC AAG AAG AAG TAC GGC AAC              528
Asp Lys Ala Arg Arg Leu Leu Trp Pro Ile Lys Lys Lys Tyr Gly Asn
                165                 170                 175

AAA ATC AGC TGG GCA GAC CTG ATG ATT CTG GCT GGC ACC GTG GCT TAT              576
Lys Ile Ser Trp Ala Asp Leu Met Ile Leu Ala Gly Thr Val Ala Tyr
            180                 185                 190

GAG TCC ATG GGC TTA CCT GCT TAC GGC TTC TCT TTC GGC CGC GTC GAT              624
Glu Ser Met Gly Leu Pro Ala Tyr Gly Phe Ser Phe Gly Arg Val Asp
        195                 200                 205

ATT TGG GAA CCC GAA AAA GAT ATC TAC TGG GGT GAC GAA AAA GAG TGG              672
Ile Trp Glu Pro Glu Lys Asp Ile Tyr Trp Gly Asp Glu Lys Glu Trp
    210                 215                 220

CTG GCA CCT TCT GAC GAA CGC TAC GGC GAC GTG AAC AAG CCA GAG ACC              720
Leu Ala Pro Ser Asp Glu Arg Tyr Gly Asp Val Asn Lys Pro Glu Thr
225                 230                 235                 240

ATG GAA AAC CCG CTG GCG GCT GTC CAA ATG GGT CTG ATC TAT GTG AAC              768
Met Glu Asn Pro Leu Ala Ala Val Gln Met Gly Leu Ile Tyr Val Asn
                245                 250                 255

CCG GAA GGT GTT AAC GGC CAC CCT GAT CCG CTG AGA ACC GCA CAG CAG              816
Pro Glu Gly Val Asn Gly His Pro Asp Pro Leu Arg Thr Ala Gln Gln
            260                 265                 270

GTA CTT GAA ACC TTC GCC CGT ATG GCG ATG AAC GAC GAA AAA ACC GCA              864
Val Leu Glu Thr Phe Ala Arg Met Ala Met Asn Asp Glu Lys Thr Ala
        275                 280                 285

GCC CTC ACA GCT GGC GGC CAC ACC GTC GGT AAT TGT CAC GGT AAT GGC              912
Ala Leu Thr Ala Gly Gly His Thr Val Gly Asn Cys His Gly Asn Gly
    290                 295                 300

AAT GCC TCT GCG TTA GCC CCT GAC CCA AAA GCC TCT GAC GTT GAA AAC              960
Asn Ala Ser Ala Leu Ala Pro Asp Pro Lys Ala Ser Asp Val Glu Asn
305                 310                 315                 320

CAG GGC TTA GGT TGG GGC AAC CCC AAC ATG CAG GGC AAG GCA AGC AAC             1008
Gln Gly Leu Gly Trp Gly Asn Pro Asn Met Gln Gly Lys Ala Ser Asn
                325                 330                 335

GCC GTG ACC TCG GGT ATC GAA GGT GCT TGG ACC ACC AAC CCC ACG AAA             1056
Ala Val Thr Ser Gly Ile Glu Gly Ala Trp Thr Thr Asn Pro Thr Lys
            340                 345                 350

TTC GAT ATG GGC TAT TTC GAC CTG CTG TTC GGC TAC AAT TGG GAA CTG             1104
Phe Asp Met Gly Tyr Phe Asp Leu Leu Phe Gly Tyr Asn Trp Glu Leu
        355                 360                 365

AAA AAG AGT CCT GCC GGT GCC CAC CAT TGG GAA CCG ATT GAC ATC AAA             1152
Lys Lys Ser Pro Ala Gly Ala His His Trp Glu Pro Ile Asp Ile Lys
    370                 375                 380

AAG GAA AAC AAG CCG GTT GAC GCC AGC GAC CCC TCT ATT CGC CAC AAC             1200
Lys Glu Asn Lys Pro Val Asp Ala Ser Asp Pro Ser Ile Arg His Asn
385                 390                 395                 400
```

| | |
|---|---|
| CCG ATC ATG ACC GAT GCG GAT ATG GCG ATA AAG GTA AAT CCG ACC TAT<br>Pro Ile Met Thr Asp Ala Asp Met Ala Ile Lys Val Asn Pro Thr Tyr<br>         405         410        415 | 1248 |
| CGC GCT ATC TGC GAA AAA TTC ATG GCC GAT CCT GAG TAC TTC AAG AAA<br>Arg Ala Ile Cys Glu Lys Phe Met Ala Asp Pro Glu Tyr Phe Lys Lys<br>     420          425        430 | 1296 |
| ACT TTC GCG AAG GCG TGG TTC AAG CTG ACG CAC CGT GAC CTG GGC CCG<br>Thr Phe Ala Lys Ala Trp Phe Lys Leu Thr His Arg Asp Leu Gly Pro<br>       435         440        445 | 1344 |
| AAA TCA CGT TAC ATC GGC CCG GAA GTG CCG GCA GAA GAC CTG ATT TGG<br>Lys Ser Arg Tyr Ile Gly Pro Glu Val Pro Ala Glu Asp Leu Ile Trp<br>450          455         460 | 1392 |
| CAA GAC CCG ATT CCG GCA GGT AAC ACC GAC TAC TGC GAA GAA GTG GTC<br>Gln Asp Pro Ile Pro Ala Gly Asn Thr Asp Tyr Cys Glu Glu Val Val<br>465          470         475        480 | 1440 |
| AAG CAG AAA ATT GCA CAA AGT GGC CTG AGC ATT AGT GAG ATG GTC TCC<br>Lys Gln Lys Ile Ala Gln Ser Gly Leu Ser Ile Ser Glu Met Val Ser<br>       485         490        495 | 1488 |
| ACC GCT TGG GAC AGT GCC CGT ACT TAT CGC GGT TCC GAT ATG CGC GGC<br>Thr Ala Trp Asp Ser Ala Arg Thr Tyr Arg Gly Ser Asp Met Arg Gly<br>     500          505        510 | 1536 |
| GGT GCT AAC GGT GCC CGC ATT CGC TTG GCC CCA CAG AAC GAG TGG CAG<br>Gly Ala Asn Gly Ala Arg Ile Arg Leu Ala Pro Gln Asn Glu Trp Gln<br>       515         520        525 | 1584 |
| GGC AAC GAG CCG GAG CGC CTG GCG AAA GTG CTG AGC GTC TAC GAG CAG<br>Gly Asn Glu Pro Glu Arg Leu Ala Lys Val Leu Ser Val Tyr Glu Gln<br>     530          535        540 | 1632 |
| ATC TCT GCC GAC ACC GGC GCT AGC ATC GCG GAC GTG ATC GTT CTG GCC<br>Ile Ser Ala Asp Thr Gly Ala Ser Ile Ala Asp Val Ile Val Leu Ala<br>545          550         555        560 | 1680 |
| GGT AGC GTA GGC ATC GAG AAA GCC GCG AAA GCA GCA GGT TAC GAT GTG<br>Gly Ser Val Gly Ile Glu Lys Ala Ala Lys Ala Ala Gly Tyr Asp Val<br>       565         570        575 | 1728 |
| CGC GTT CCC TTC CTG AAA GGC CGT GGC GAT GCG ACC GCC GAG ATG ACC<br>Arg Val Pro Phe Leu Lys Gly Arg Gly Asp Ala Thr Ala Glu Met Thr<br>     580          585        590 | 1776 |
| GAC GCA GAC TCC TTC GCA CCG CTG GAG CCG CTG GCC GAT GGC TTC CGC<br>Asp Ala Asp Ser Phe Ala Pro Leu Glu Pro Leu Ala Asp Gly Phe Arg<br>       595         600        605 | 1824 |
| AAC TGG CAG AAG AAA GAG TAT GTG GTG AAG CCG GAA GAG ATG CTG CTG<br>Asn Trp Gln Lys Lys Glu Tyr Val Val Lys Pro Glu Glu Met Leu Leu<br>     610          615        620 | 1872 |
| GAT CGT GCG CAG CTG ATG GGC TTA ACC GGC CCG GAA ATG ACC GTG CTG<br>Asp Arg Ala Gln Leu Met Gly Leu Thr Gly Pro Glu Met Thr Val Leu<br>625          630         635        640 | 1920 |
| CTG GGC GGT ATG CGC GTA CTG GGC ACC AAC TAT GGT GGC ACC AAA CAC<br>Leu Gly Gly Met Arg Val Leu Gly Thr Asn Tyr Gly Gly Thr Lys His<br>       645         650        655 | 1968 |
| GGC GTA TTC ACC GAT TGT GAA GGC CAG TTG ACC AAC GAC TTT TTT GTG<br>Gly Val Phe Thr Asp Cys Glu Gly Gln Leu Thr Asn Asp Phe Phe Val<br>     655          660        665 | 2016 |
| AAC CTG ACC GAT ATG GGG AAC AGC TGG AAG CCG GTA GGT AGC AAC GCC<br>Asn Leu Thr Asp Met Gly Asn Ser Trp Lys Pro Val Gly Ser Asn Ala<br>     670          675        680 | 2064 |
| TAC GAA ATC CGC GAC CGC AAG ACC GGT GCC GTG AAG TGG ACC GCC TCG<br>Tyr Glu Ile Arg Asp Arg Lys Thr Gly Ala Val Lys Trp Thr Ala Ser<br>     685          690        700 | 2112 |
| CGG GTG GAT CTG GTA TTT GGT TCC AAC TCG CTA CTG CGC TCT TAC GCA<br>Arg Val Asp Leu Val Phe Gly Ser Asn Ser Leu Leu Arg Ser Tyr Ala<br>705          710         715        720 | 2160 |

```
GAA GTG TAC GCC CAG GAC GAT AAC GGC GAG AAG TTC GTC AGA GAC TTC    2208
Glu Val Tyr Ala Gln Asp Asp Asn Gly Glu Lys Phe Val Arg Asp Phe
                725                 730                 735

GTC GCC GCC TGG ACC AAA GTG ATG AAC GCC GAC CGT TTC GAC GTC GCG    2256
Val Ala Ala Trp Thr Lys Val Met Asn Ala Asp Arg Phe Asp Val Ala
            740                 745                 750

TCG TAA                                                            2262
Ser
```

(2) INFORMATION FOR SEQ ID NO:6:

(i) SEQUENCE CHARACTERISTICS:
        (A) LENGTH: 753 AMINO ACIDS (B) TYPE: AMINO ACID (D) TOPOLOGY: LINEAR (ii) MOLECULE TYPE: Polypeptide (xi) SEQUENCE DESCRIPTION: SEQ ID NO:6:

```
Met Asn Asn Ala Ser Ala Asp Asp Leu His Ser Ser Leu Gln Gln Arg
                  5                  10                  15

Cys Arg Ala Phe Val Pro Leu Val Ser Pro Arg His Arg Ala Ile Arg
             20                  25                  30

Glu Arg Ala Met Ser Gly Lys Cys Pro Val Met His Gly Gly Asn Thr
         35                  40                  45

Ser Thr Gly Thr Ser Asn Lys Asp Trp Trp Pro Glu Gly Leu Asn Leu
 50                  55                  60

Asp Ile Leu His Gln Gln Asp Arg Lys Ser Asp Pro Met Asp Pro Asp
65                  70                  75                  80

Phe Asn Tyr Arg Glu Glu Val Arg Lys Leu Asp Phe Asp Ala Leu Lys
                 85                  90                  95

Lys Asp Val His Ala Leu Met Thr Asp Ser Gln Glu Trp Trp Pro Ala
            100                 105                 110

Asp Trp Gly His Tyr Gly Gly Leu Met Ile Arg Met Ala Trp His Ser
        115                 120                 125

Ala Gly Thr Tyr Arg Ile Ala Asp Gly Arg Gly Gly Gly Thr Gly
    130                 135                 140

Ser Gln Arg Phe Ala Pro Leu Asn Ser Trp Pro Asp Asn Val Ser Leu
145                 150                 155                 160

Asp Lys Ala Arg Arg Leu Leu Trp Pro Ile Lys Lys Tyr Gly Asn
                165                 170                 175

Lys Ile Ser Trp Ala Asp Leu Met Ile Leu Ala Gly Thr Val Ala Tyr
            180                 185                 190

Glu Ser Met Gly Leu Pro Ala Tyr Gly Phe Ser Phe Gly Arg Val Asp
        195                 200                 205

Ile Trp Glu Pro Glu Lys Asp Ile Tyr Trp Gly Asp Glu Lys Glu Trp
    210                 215                 220

Leu Ala Pro Ser Asp Glu Arg Tyr Gly Asp Val Asn Lys Pro Glu Thr
225                 230                 235                 240

Met Glu Asn Pro Leu Ala Ala Val Gln Met Gly Leu Ile Tyr Val Asn
                245                 250                 255

Pro Glu Gly Val Asn Gly His Pro Asp Pro Leu Arg Thr Ala Gln Gln
            260                 265                 270

Val Leu Glu Thr Phe Ala Arg Met Ala Met Asn Asp Glu Lys Thr Ala
```

-continued

```
              275                 280                 285
Ala Leu Thr Ala Gly Gly His Thr Val Gly Asn Cys His Gly Asn Gly
    290                 295                 300
Asn Ala Ser Ala Leu Ala Pro Asp Pro Lys Ala Ser Asp Val Glu Asn
305                 310                 315                 320
Gln Gly Leu Gly Trp Gly Asn Pro Asn Met Gln Gly Lys Ala Ser Asn
                325                 330                 335
Ala Val Thr Ser Gly Ile Glu Gly Ala Trp Thr Thr Asn Pro Thr Lys
            340                 345                 350
Phe Asp Met Gly Tyr Phe Asp Leu Leu Phe Gly Tyr Asn Trp Glu Leu
        355                 360                 365
Lys Lys Ser Pro Ala Gly Ala His His Trp Glu Pro Ile Asp Ile Lys
370                 375                 380
Lys Glu Asn Lys Pro Val Asp Ala Ser Asp Pro Ser Ile Arg His Asn
385                 390                 395                 400
Pro Ile Met Thr Asp Ala Asp Met Ala Ile Lys Val Asn Pro Thr Tyr
                405                 410                 415
Arg Ala Ile Cys Glu Lys Phe Met Ala Asp Pro Glu Tyr Phe Lys Lys
            420                 425                 430
Thr Phe Ala Lys Ala Trp Phe Lys Leu Thr His Arg Asp Leu Gly Pro
        435                 440                 445
Lys Ser Arg Tyr Ile Gly Pro Glu Val Pro Ala Glu Asp Leu Ile Trp
    450                 455                 460
Gln Asp Pro Ile Pro Ala Gly Asn Thr Asp Tyr Cys Glu Glu Val Val
465                 470                 475                 480
Lys Gln Lys Ile Ala Gln Ser Gly Leu Ser Ile Ser Glu Met Val Ser
                485                 490                 495
Thr Ala Trp Asp Ser Ala Arg Thr Tyr Arg Gly Ser Asp Met Arg Gly
            500                 505                 510
Gly Ala Asn Gly Ala Arg Ile Arg Leu Ala Pro Gln Asn Glu Trp Gln
        515                 520                 525
Gly Asn Glu Pro Glu Arg Leu Ala Lys Val Leu Ser Val Tyr Glu Gln
    530                 535                 540
Ile Ser Ala Asp Thr Gly Ala Ser Ile Ala Asp Val Ile Val Leu Ala
545                 550                 555                 560
Gly Ser Val Gly Ile Glu Lys Ala Ala Lys Ala Ala Gly Tyr Asp Val
                565                 570                 575
Arg Val Pro Phe Leu Lys Gly Arg Gly Asp Ala Thr Ala Glu Met Thr
            580                 585                 590
Asp Ala Asp Ser Phe Ala Pro Leu Glu Pro Leu Ala Asp Gly Phe Arg
        595                 600                 605
Asn Trp Gln Lys Lys Glu Tyr Val Val Lys Pro Glu Glu Met Leu Leu
    610                 615                 620
Asp Arg Ala Gln Leu Met Gly Leu Thr Gly Pro Glu Met Thr Val Leu
625                 630                 635                 640
Leu Gly Gly Met Arg Val Leu Gly Thr Asn Tyr Gly Gly Thr Lys His
                645                 650                 655
Gly Val Phe Thr Asp Cys Glu Gly Gln Leu Thr Asn Asp Phe Phe Val
            660                 665                 670
Asn Leu Thr Asp Met Gly Asn Ser Trp Lys Pro Val Gly Ser Asn Ala
        675                 680                 685
Tyr Glu Ile Arg Asp Arg Lys Thr Gly Ala Val Lys Trp Thr Ala Ser
    690                 695                 700
```

-continued

```
Arg Val Asp Leu Val Phe Gly Ser Asn Ser Leu Leu Arg Ser Tyr Ala
705                 710                 715                 720

Glu Val Tyr Ala Gln Asp Asp Asn Gly Glu Lys Phe Val Arg Asp Phe
            725                 730                 735

Val Ala Ala Trp Thr Lys Val Met Asn Ala Asp Arg Phe Asp Val Ala
        740                 745                 750

Ser
```

(2) INFORMATION FOR SEQ ID NO:7:

(i) SEQUENCE CHARACTERISTICS:
        (A) LENGTH: 2238 NUCLEOTIDES (B) TYPE: NUCLEIC ACID (C) STRANDEDNESS: SINGLE (D) TOPOLOGY: LINEAR (ii) MOLECULE TYPE: DNA (xi) SEQUENCE DESCRIPTION: SEQ ID NO:7:

```
ATG GAA AAT CAC AAA CAC TCA GGA TCT TCT ACG TAT AAC ACA AAC ACT        48
Met Glu Asn His Lys His Ser Gly Ser Ser Thr Tyr Asn Thr Asn Thr
                5                  10                  15

GGC GGA AAA TGC CCT TTT ACC GGA GGT TCG CTT AAG CAA AGT GCA GGT        96
Gly Gly Lys Cys Pro Phe Thr Gly Gly Ser Leu Lys Gln Ser Ala Gly
            20                  25                  30

GGC GGC ACC AAA AAC AGG GAT TGG TGG CCC AAC ATG CTC AAC CTC GGC       144
Gly Gly Thr Lys Asn Arg Asp Trp Trp Pro Asn Met Leu Asn Leu Gly
        35                  40                  45

ATC TTA CGC CAA CAT TCA TCG CTA TCG GAC CCA AAC GAC CCG GAT TTT       192
Ile Leu Arg Gln His Ser Ser Leu Ser Asp Pro Asn Asp Pro Asp Phe
    50                  55                  60

GAC TAT GCC GAA GAG TTT AAG AAG CTA GAT CTG GCA GCG GTT AAA AAG       240
Asp Tyr Ala Glu Glu Phe Lys Lys Leu Asp Leu Ala Ala Val Lys Lys
65                  70                  75                  80

GAC CTG GCA GCG CTA ATG ACA GAT TCA CAG GAC TGG TGG CCA GCA GAT       288
Asp Leu Ala Ala Leu Met Thr Asp Ser Gln Asp Trp Trp Pro Ala Asp
                85                  90                  95

TAC GGT CAT TAT GGC CCC TTC TTT ATA CGC ATG GCG TGG CAC AGC GCC       336
Tyr Gly His Tyr Gly Pro Phe Phe Ile Arg Met Ala Trp His Ser Ala
            100                 105                 110

GGC ACC TAC CGT ATC GGT GAT GGC CGT GGT GGC GGT GGC TCC GGC TCA       384
Gly Thr Tyr Arg Ile Gly Asp Gly Arg Gly Gly Gly Gly Ser Gly Ser
        115                 120                 125

CAG CGC TTC GCG CCT CTC AAT AGC TGG CCA GAC AAT GCC AAT CTG GAT       432
Gln Arg Phe Ala Pro Leu Asn Ser Trp Pro Asp Asn Ala Asn Leu Asp
    130                 135                 140

AAA GCA CGC TTG CTT CTT TGG CCC ATC AAA CAA AAA TAC GGT CGA AAA       480
Lys Ala Arg Leu Leu Leu Trp Pro Ile Lys Gln Lys Tyr Gly Arg Lys
145                 150                 155                 160

ATC TCC TGG GCG GAT CTA ATG ATA CTC ACA GGA AAC GTA GCT CTG GAA       528
Ile Ser Trp Ala Asp Leu Met Ile Leu Thr Gly Asn Val Ala Leu Glu
                165                 170                 175

ACT ATG GGC TTT AAA ACT TTT GGT TTT GCA GGT GGC AGA GCA GAT GTA       576
Thr Met Gly Phe Lys Thr Phe Gly Phe Ala Gly Gly Arg Ala Asp Val
            180                 185                 190

TGG GAG CCT GAA GAA GAT GTA TAC TGG GGA GCA GAA ACC GAA TGG CTG       624
Trp Glu Pro Glu Glu Asp Val Tyr Trp Gly Ala Glu Thr Glu Trp Leu
```

-continued

```
            195                 200                 205
GGA GAC AAG CGC TAT GAA GGT GAC CGA GAG CTC GAA AAT CCC CTG GGA         672
Gly Asp Lys Arg Tyr Glu Gly Asp Arg Glu Leu Glu Asn Pro Leu Gly
    210                 215                 220

GCC GTA CAA ATG GGA CTC ATC TAT GTA AAC CCC GAA GGA CCC AAC GGC         720
Ala Val Gln Met Gly Leu Ile Tyr Val Asn Pro Glu Gly Pro Asn Gly
225                 230                 235                 240

AAG CCA GAC CCT ATC GCT GCT GCG CGT GAT ATT CGT GAG ACT TTT GGC         768
Lys Pro Asp Pro Ile Ala Ala Ala Arg Asp Ile Arg Glu Thr Phe Gly
                245                 250                 255

CGA ATG GCA ATG AAT GAC GAA GAA ACC GTG GCT CTC ATA GCG GGT GGA         816
Arg Met Ala Met Asn Asp Glu Glu Thr Val Ala Leu Ile Ala Gly Gly
            260                 265                 270

CAC ACC TTC GGA AAA ACC CAT GGT GCT GCC GAT GCG GAG AAA TAT GTG         864
His Thr Phe Gly Lys Thr His Gly Ala Ala Asp Ala Glu Lys Tyr Val
        275                 280                 285

GGC CGA GAG CCT GCC GCC GCA GGT ATT GAA GAA ATG AGC CTG GGG TGG         912
Gly Arg Glu Pro Ala Ala Ala Gly Ile Glu Glu Met Ser Leu Gly Trp
    290                 295                 300

AAA AAC ACC TAC GGC ACC GGA CAC GGT GCG GAT ACC ATC ACC AGT GGA         960
Lys Asn Thr Tyr Gly Thr Gly His Gly Ala Asp Thr Ile Thr Ser Gly
305                 310                 315                 320

CTA GAA GGC GCC TGG ACC AAG ACC CCT ACT CAA TGG AGC AAT AAC TTT        1008
Leu Glu Gly Ala Trp Thr Lys Thr Pro Thr Gln Trp Ser Asn Asn Phe
                325                 330                 335

TTT GAA AAC CTC TTT GGT TAC GAG TGG GAG CTT ACC AAA AGT CCA GCT        1056
Phe Glu Asn Leu Phe Gly Tyr Glu Trp Glu Leu Thr Lys Ser Pro Ala
            340                 345                 350

GGA GCT TAT CAG TGG AAA CCA AAA GAC GGT GCC GGG GCT GGC ACC ATA        1104
Gly Ala Tyr Gln Trp Lys Pro Lys Asp Gly Ala Gly Ala Gly Thr Ile
        355                 360                 365

CCG GAT GCA CAT GAT CCC AGC AAG TCG CAC GCT CCA TTT ATG CTC ACT        1152
Pro Asp Ala His Asp Pro Ser Lys Ser His Ala Pro Phe Met Leu Thr
    370                 375                 380

ACG GAC CTG GCG CTG CGC ATG GAC CCT GAT TAC GAA AAA ATT TCT CGA        1200
Thr Asp Leu Ala Leu Arg Met Asp Pro Asp Tyr Glu Lys Ile Ser Arg
385                 390                 395                 400

CGG TAC TAT GAA AAC CCT GAT GAG TTT GCA GAT GCT TTC GCG AAA GCA        1248
Arg Tyr Tyr Glu Asn Pro Asp Glu Phe Ala Asp Ala Phe Ala Lys Ala
                405                 410                 415

TGG TAC AAA CTG ACA CAC AGA GAT ATG GGA CCA AAG GTG CGC TAC CTG        1296
Trp Tyr Lys Leu Thr His Arg Asp Met Gly Pro Lys Val Arg Tyr Leu
            420                 425                 430

GGA CCA GAA GTG CCT CAG GAA GAC CTC ATC TGG CAA GAC CCT ATA CCA        1344
Gly Pro Glu Val Pro Gln Glu Asp Leu Ile Trp Gln Asp Pro Ile Pro
        435                 440                 445

GAT GTA AGC CAT CCT CTT GTA GAC GAA AAC GAT ATT GAA GGC CTA AAA        1392
Asp Val Ser His Pro Leu Val Asp Glu Asn Asp Ile Glu Gly Leu Lys
    450                 455                 460

GCC AAA ATC CTG GAA TCG GGA CTG ACG GTA AGC GAG CTG GTA AGC ACG        1440
Ala Lys Ile Leu Glu Ser Gly Leu Thr Val Ser Glu Leu Val Ser Thr
465                 470                 475                 480

GCA TGG GCT TCT GCA TCT ACT TTT AGA AAC TCT GAC AAG CGC GGC GGT        1488
Ala Trp Ala Ser Ala Ser Thr Phe Arg Asn Ser Asp Lys Arg Gly Gly
                485                 490                 500

GCC AAC GGT GCA CGT ATA CGA CTG GCC CCA CAA AAA GAC TGG GAA GTA        1536
Ala Asn Gly Ala Arg Ile Arg Leu Ala Pro Gln Lys Asp Trp Glu Val
            505                 510                 515

AAC AAC CCT CAG CAA CTT GCC AGG GTA CTC AAA ACA CTA GAA GGT ATC        1584
```

```
Asn Asn Pro Gln Gln Leu Ala Arg Val Leu Lys Thr Leu Glu Gly Ile
        520                 525                 530

CAG GAG GAC TTT AAC CAG GCG CAA TCA GAT AAC AAA GCA GTA TCG TTG         1632
Gln Glu Asp Phe Asn Gln Ala Gln Ser Asp Asn Lys Ala Val Ser Leu
535             540                 545

GCC GAC CTG ATT GTG CTG GCC GGC TGT GCG GGT GTA GAA AAA GCT GCA         1680
Ala Asp Leu Ile Val Leu Ala Gly Cys Ala Gly Val Glu Lys Ala Ala
550                 555                 560                 565

AAA GAT GCT GGC CAT GAG GTG CAG GTG CCT TTC AAC CCG GGA CGA GCG         1728
Lys Asp Ala Gly His Glu Val Gln Val Pro Phe Asn Pro Gly Arg Ala
            570                 575                 580

GAT GCC ACC GCT GAG CAA ACC GAT GTG GAA GCT TTC GAA GCA CTA GAG         1776
Asp Ala Thr Ala Glu Gln Thr Asp Val Glu Ala Phe Glu Ala Leu Glu
                585                 590                 595

CCA GCG GCT GAC GGC TTT AGA AAC TAC ATT AAA CCG GAG CAT AAA GTA         1824
Pro Ala Ala Asp Gly Phe Arg Asn Tyr Ile Lys Pro Glu His Lys Val
                    600                 605                 610

TCC GCT GAG GAA ATG CTC GTA GAC CGG GCG CAG CTT CTG TCG CTT TCG         1872
Ser Ala Glu Glu Met Leu Val Asp Arg Ala Gln Leu Leu Ser Leu Ser
                        615                 620                 625

GCA CCA GAA ATG ACT GCT TTG GTA GGC GGT ATG CGT GTA CTG GGC ACC         1920
Ala Pro Glu Met Thr Ala Leu Val Gly Gly Met Arg Val Leu Gly Thr
630                 635                 640                 645

AAC TAC GAC GGT TCG CAG CAT GGA GTG TTT ACA AAT AAG CCG GGT CAG         1968
Asn Tyr Asp Gly Ser Gln His Gly Val Phe Thr Asn Lys Pro Gly Gln
                650                 655                 660

CTA TCC AAT GAC TTC TTT GTA AAC CTG CTA GAC CTC AAC ACT AAA TGG         2016
Leu Ser Asn Asp Phe Phe Val Asn Leu Leu Asp Leu Asn Thr Lys Trp
                    665                 670                 675

CGA GCC AGC GAT GAA TCA GAC AAA GTT TTT GAA GGC AGA GAC TTC AAA         2064
Arg Ala Ser Asp Glu Ser Asp Lys Val Phe Glu Gly Arg Asp Phe Lys
                        680                 685                 690

ACT GGC GAA GTA AAG TGG AGT GGC ACC CGG GTA GAC CTG ATC TTC GGA         2112
Thr Gly Glu Val Lys Trp Ser Gly Thr Arg Val Asp Leu Ile Phe Gly
695                 700                 705                 710

TCC AAT TCC GAG CTA AGA GCC CTC GCA GAA GTG TAC GGC TGT GCA GAT         2160
Ser Asn Ser Glu Leu Arg Ala Leu Ala Glu Val Tyr Gly Cys Ala Asp
715                 720                 725                 730

TCT GAA GAA AAG TTT GTT AAA GAT TTT GTG AAG GCC TGG GCC AAA GTA         2208
Ser Glu Glu Lys Phe Val Lys Asp Phe Val Lys Ala Trp Ala Lys Val
                735                 740                 745

ATG GAC CTG GAC CGG TTT GAT CTG AAA TAA                                 2238
Met Asp Leu Asp Arg Phe Asp Leu Lys
            750                 755

(2) INFORMATION FOR SEQ ID NO:8:

(i) SEQUENCE CHARACTERISTICS:
        (A) LENGTH: 745 AMINO ACIDS (B) TYPE: AMINO ACID (D) TOPOLOGY: LINEAR (ii) MOLECULE TYPE:

(xi) SEQUENCE DESCRIPTION: SEQ ID NO:8:

Met Glu Asn His Lys His Ser Gly Ser Ser Thr Tyr Asn Thr Asn Thr
                5                   10                  15

Gly Gly Lys Cys Pro Phe Thr Gly Gly Ser Leu Lys Gln Ser Ala Gly
            20                  25                  30
```

-continued

Gly Gly Thr Lys Asn Arg Asp Trp Trp Pro Asn Met Leu Asn Leu Gly
         35                  40                  45

Ile Leu Arg Gln His Ser Ser Leu Ser Asp Pro Asn Asp Pro Asp Phe
 50                  55                  60

Asp Tyr Ala Glu Glu Phe Lys Lys Leu Asp Leu Ala Ala Val Lys Lys
 65                  70                  75                  80

Asp Leu Ala Ala Leu Met Thr Asp Ser Gln Asp Trp Trp Pro Ala Asp
                 85                  90                  95

Tyr Gly His Tyr Gly Pro Phe Phe Ile Arg Met Ala Trp His Ser Ala
             100                 105                 110

Gly Thr Tyr Arg Ile Gly Asp Gly Arg Gly Gly Gly Ser Gly Ser
         115                 120                 125

Gln Arg Phe Ala Pro Leu Asn Ser Trp Pro Asp Asn Ala Asn Leu Asp
 130                 135                 140

Lys Ala Arg Leu Leu Leu Trp Pro Ile Lys Gln Lys Tyr Gly Arg Lys
145                 150                 155                 160

Ile Ser Trp Ala Asp Leu Met Ile Leu Thr Gly Asn Val Ala Leu Glu
                 165                 170                 175

Thr Met Gly Phe Lys Thr Phe Gly Phe Ala Gly Gly Arg Ala Asp Val
             180                 185                 190

Trp Glu Pro Glu Glu Asp Val Tyr Trp Gly Ala Glu Thr Glu Trp Leu
         195                 200                 205

Gly Asp Lys Arg Tyr Glu Gly Asp Arg Glu Leu Glu Asn Pro Leu Gly
         210                 215                 220

Ala Val Gln Met Gly Leu Ile Tyr Val Asn Pro Glu Gly Pro Asn Gly
225                 230                 235                 240

Lys Pro Asp Pro Ile Ala Ala Ala Arg Asp Ile Arg Glu Thr Phe Gly
                 245                 250                 255

Arg Met Ala Met Asn Asp Glu Thr Val Ala Leu Ile Ala Gly Gly
             260                 265                 270

His Thr Phe Gly Lys Thr His Gly Ala Ala Asp Ala Glu Lys Tyr Val
         275                 280                 285

Gly Arg Glu Pro Ala Ala Ala Gly Ile Glu Glu Met Ser Leu Gly Trp
 290                 295                 300

Lys Asn Thr Tyr Gly Thr Gly His Gly Ala Asp Thr Ile Thr Ser Gly
305                 310                 315                 320

Leu Glu Gly Ala Trp Thr Lys Thr Pro Thr Gln Trp Ser Asn Asn Phe
                 325                 330                 335

Phe Glu Asn Leu Phe Gly Tyr Glu Trp Glu Leu Thr Lys Ser Pro Ala
             340                 345                 350

Gly Ala Tyr Gln Trp Lys Pro Lys Asp Gly Ala Gly Ala Gly Thr Ile
         355                 360                 365

Pro Asp Ala His Asp Pro Ser Lys Ser His Ala Pro Phe Met Leu Thr
 370                 375                 380

Thr Asp Leu Ala Leu Arg Met Asp Pro Asp Tyr Glu Lys Ile Ser Arg
385                 390                 395                 400

Arg Tyr Tyr Glu Asn Pro Asp Glu Phe Ala Asp Ala Phe Ala Lys Ala
                 405                 410                 415

Trp Tyr Lys Leu Thr His Arg Asp Met Gly Pro Lys Val Arg Tyr Leu
             420                 425                 430

Gly Pro Glu Val Pro Gln Glu Asp Leu Ile Trp Gln Asp Pro Ile Pro
         435                 440                 445

-continued

```
Asp Val Ser His Pro Leu Val Asp Glu Asn Asp Ile Glu Gly Leu Lys
    450                 455                 460
Ala Lys Ile Leu Glu Ser Gly Leu Thr Val Ser Glu Leu Val Ser Thr
465                 470                 475                 480
Ala Trp Ala Ser Ala Ser Thr Phe Arg Asn Ser Asp Lys Arg Gly Gly
                485                 490                 495
Ala Asn Gly Ala Arg Ile Arg Leu Ala Pro Gln Lys Asp Trp Glu Val
            500                 505                 510
Asn Asn Pro Gln Gln Leu Ala Arg Val Leu Lys Thr Leu Glu Gly Ile
        515                 520                 525
Gln Glu Asp Phe Asn Gln Ala Gln Ser Asp Asn Lys Ala Val Ser Leu
    530                 535                 540
Ala Asp Leu Ile Val Leu Ala Gly Cys Ala Gly Val Glu Lys Ala Ala
545                 550                 555                 560
Lys Asp Ala Gly His Glu Val Gln Val Pro Phe Asn Pro Gly Arg Ala
                565                 570                 575
Asp Ala Thr Ala Glu Gln Thr Asp Val Glu Ala Phe Glu Ala Leu Glu
            580                 585                 590
Pro Ala Ala Asp Gly Phe Arg Asn Tyr Ile Lys Pro Glu His Lys Val
        595                 600                 605
Ser Ala Glu Glu Met Leu Val Asp Arg Ala Gln Leu Leu Ser Leu Ser
    610                 615                 620
Ala Pro Glu Met Thr Ala Leu Val Gly Gly Met Arg Val Leu Gly Thr
625                 630                 635                 640
Asn Tyr Asp Gly Ser Gln His Gly Val Phe Thr Asn Lys Pro Gly Gln
                645                 650                 655
Leu Ser Asn Asp Phe Phe Val Asn Leu Leu Asp Leu Asn Thr Lys Trp
            660                 665                 670
Arg Ala Ser Asp Glu Ser Asp Lys Val Phe Glu Gly Arg Asp Phe Lys
        675                 680                 685
Thr Gly Glu Val Lys Trp Ser Gly Thr Arg Val Asp Leu Ile Phe Gly
    690                 695                 700
Ser Asn Ser Glu Leu Arg Ala Leu Ala Glu Val Tyr Gly Cys Ala Asp
705                 710                 715                 720
Ser Glu Glu Lys Phe Val Lys Asp Phe Val Lys Ala Trp Ala Lys Val
                725                 730                 735
Met Asp Leu Asp Arg Phe Asp Leu Lys
            740                 745
```